United States Patent [19]

Sosniak et al.

[11] 4,224,565

[45] Sep. 23, 1980

[54] MOISTURE LEVEL DETERMINATION IN SEALED PACKAGES

[75] Inventors: Jacob Sosniak, Millburn; Burton A. Unger, Berkeley Heights, both of N.J.

[73] Assignee: Bell Telephone Laboratories, Incorporated, Murray Hill, N.J.

[21] Appl. No.: 912,472

[22] Filed: Jun. 5, 1978

[51] Int. Cl.² .................... G01R 27/02; G01R 27/26; H01C 13/00

[52] U.S. Cl. ............................... 324/65 R; 73/336.5; 324/61 R; 338/35

[58] Field of Search ................. 324/65 R, 61 C, 57 R, 324/71 SN, 62, 65 P, 61 P, 61 R; 340/602, 604; 338/35; 73/17 R, 17 A, 336.5, 344

[56] References Cited

U.S. PATENT DOCUMENTS

| | | | |
|---|---|---|---|
| 2,713,625 | 7/1955 | Johnson et al. | 338/35 |
| 3,139,085 | 6/1964 | Custance et al. | 324/65 X |
| 3,255,324 | 6/1966 | Ovshinsky | 324/71 SN |
| 3,315,518 | 4/1967 | Charlson et al. | 338/35 X |
| 3,705,375 | 12/1972 | Hershler | 338/35 |
| 3,943,557 | 3/1976 | Frazee et al. | 324/65 R X |
| 4,083,030 | 4/1978 | Groninger | 338/35 |
| 4,107,555 | 8/1978 | Haas et al. | 324/61 R X |
| 4,127,763 | 11/1978 | Roselli | 338/35 X |

OTHER PUBLICATIONS

Kovac et al, A New Moisture Sensor for In-Situ Monitoring of Sealed Packages, Solid State Technology, Feb. 1978, pp. 35-39, 53.

Busick, R. C., "Electronic Measurement...", 1965, MS Thesis Ohio State Univ.

Wexler, A., Humidity and Moisture, 1965, pp. 428-432, vol. 2, Reinhold Publications.

Wexler, A., Humidity and Moisture, 1965, vol. 4, pp. 113-117, Reinhold Publications.

*Primary Examiner*—Ernest F. Karlsen
*Attorney, Agent, or Firm*—Lucian C. Canepa

[57] ABSTRACT

A moisture sensing unit (30, FIG. 1 or 58, FIG. 4) is included within a hermetically sealed package. A localized external portion of the package in close proximity to the unit is cooled while the temperature and the alternating-current capacitance and/or conductance characteristic of the unit are measured. The measured characteristic exhibits a sharp increase at the temperature corresponding to the dew point of the atmosphere within the package. In turn, the dew point temperature is a direct indicator of the moisture content of the package.

9 Claims, 5 Drawing Figures

MOISTURE LEVEL DETERMINATION IN SEALED PACKAGES

TECHNICAL FIELD

This invention relates to measuring the moisture content of the atmosphere within a closed container and, more particularly, to techniques for measuring moisture levels in hermetically sealed microelectronic device packages.

BACKGROUND OF THE INVENTION

It is well known that various types of device failures are attributable to the presence of moisture. Thus, for example, in sealed packages containing microelectronic devices of the integrated-circuit type, a water vapor concentration as low as several thousand parts per million can cause device failures. Accordingly, efforts have been directed at devising techniques for measuring the moisture level within such a package. By determining this level during the device fabrication process, it is possible initially to identify and reject failure-prone sealed packages. Moreover, by subsequently monitoring the moisture level within packages actually connected in working equipment, it is feasible to identify and replace those packages whose moisture content later rises above acceptable limits due to leakage or to outgassing of materials within the package.

Heretofore, various types of in-situ moisture sensors for inclusion in sealed packages have been suggested. One such known sensor comprises a pair of interdigitated electrodes contained within the package. During a moisture measuring cycle, the entire package is placed in a test chamber whose ambient temperature can be controlled. As the package is cooled, the direct-current conductivity between the electrodes of the sensor is measured. When the dew point of the atmosphere within the package is reached, moisture condenses on the electrodes. At that point, an increase in conductivity between the electrodes is detected. From such a determination of the dew point temperature within the package, the water vapor concentration therein may be directly determined. A dew point moisture sensor of this type is described in "A New Moisture Sensor for In-Situ Monitoring of Sealed Packages", *Solid State Technology*, February 1978, pages 35-39, 53.

Although the above-described dew point moisture sensor for sealed packages appeared in concept to be attractive, it was found in practice to be insufficiently sensitive and accurate for performing critical low-moisture measurements. Accordingly, applicants and other workers in the field continued to try to devise moisture measuring techniques which would exhibit improved sensitivity and accuracy.

SUMMARY OF THE INVENTION

In accordance with a basic aspect of the principles of the present invention, applicants recognized that a dew point sensor could in fact be the basis for performing a sensitive and accurate measurement of moisture within a sealed package. To successfully perform such a measurement, applicants modified known techniques in several unique and unobvious ways. The improved assembly and measurement method devised by applicants constitute an effective way of determining moisture levels in sealed microelectronic device packages.

In accordance with one specific aspect of applicants' invention, a dew point sensor is included in a sealed package as an integral part thereof. A localized external portion of the package in close proximity to the unit is cooled, so as to greatly enhance the collection of moisture while the temperature and the alternating-current capacitance and/or conductance characteristic of the unit are measured. The measured characteristic exhibits a sharp increase at the temperature corresponding to the dew point of the atmosphere within the package. In turn, this point is a direct indicator of the moisture content of the package.

In one specific aspect, applicants' invention comprises an electrical assembly including a housing, an interior sealed compartment defined by said housing, and plural conductive elements mounted in the housing. Each of the elements includes an interior end extending into the compartment and an exterior end extending outside of the housing. Further, the assembly includes a moisture sensing unit in the compartment. Advantageously, the assembly is characterized in that the housing includes an exterior recess in close proximity to and in aligned registry with the unit, the recess being adapted to receive therein a cooling head. Moreover, the assembly is further characterized in that the sensing unit comprises first and second spaced-apart conductive members and in that the first conductive member is electrically connected to the interior end of one of the conductive elements and the ends of the second conductive member are respectively connected to the interior ends of two other conductive elements.

In another specific aspect, applicants' invention comprises a method for measuring the moisture content of the atmosphere within a sealed package that contains therein a sensing unit. The method comprises the steps of decreasing the temperature of the package to condense moisture on the unit when the dew point temperature is reached, measuring the alternating-current capacitance and/or conductance of the unit as the temperature is decreased below the normal ambient within the package, detecting the temperature at which the capacitance and/or conductance of the unit rises above the value that is characteristic of the unit at the normal ambient temperature, and determining the moisture content of the package from the detected temperature which is the dew point of the atmosphere within the package.

BRIEF DESCRIPTION OF THE DRAWING

A complete understanding of the present invention and of the above and other features thereof may be gained from a consideration of the following detailed description presented hereinbelow in connection with the accompanying drawing, in which.

DETAILED DESCRIPTION

Figure 1:
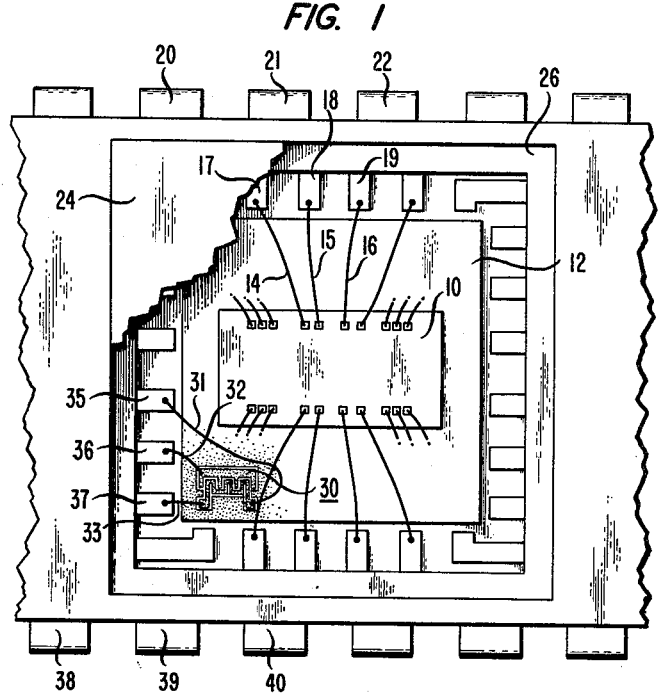
FIG. 1 is a top view of a portion of a microelectronic device package that includes therein a sensing unit adapted to be utilized in carrying out moisture measurements in accordance with the principles of the present invention.

In FIG. 1 a standard integrated circuit chip 10 is shown mounted and wired in place in a conventional ceramic package which is intended to be hermetically sealed. By way of example, the chip 10 is assumed to have been eutectically bonded to a gold film 12 deposited on the entire bottom surface of a recessed interior portion of the package. Lengths of conductive wire (such as those designated 14, 15, 16 . . .) are respectively bonded between pads on the chip 10 and conductive interior terminal portions 17, 18, 19 . . . In turn, each of the portions 17, 18, 19 . . . extends through a wall of the depicted package and appears exteriorly thereof as an electrical terminal. Thus, for example, exterior terminals 20, 21, and 22 are electrically connected to the interior portions 17, 18, and 19, respectively. By means of these exterior terminals, the integrated circuit on the chip 10 can be connected to other components in an electrical assembly, in a manner well known in the art.

The package of FIG. 1 also includes a cover 24 most of which has been broken away in the drawing so as to reveal the aforedescribed interior region. In the process of sealing the package, the cover 24 is bonded in place on a recessed shelf 26 in any one of various standard ways.

In accordance with one specific aspect of the principles of the present invention, a moisture sensing unit 30 (FIG. 1) is formed in the gold film 12 by, for example, standard laser machining techniques. In one particular illustrative embodiment, the unit 30 comprises a three-terminal element. In that case, three wire leads 31 through 33 respectively extend between the three terminals of the unit 30 and three interior terminal portions 35 through 37. In turn, these portions 35 through 37 are electrically connected to three respective exterior terminals 38 through 40. By means of these exterior terminals, electrical access to the unit 30 is realized once the depicted package is sealed.

Figure 2:
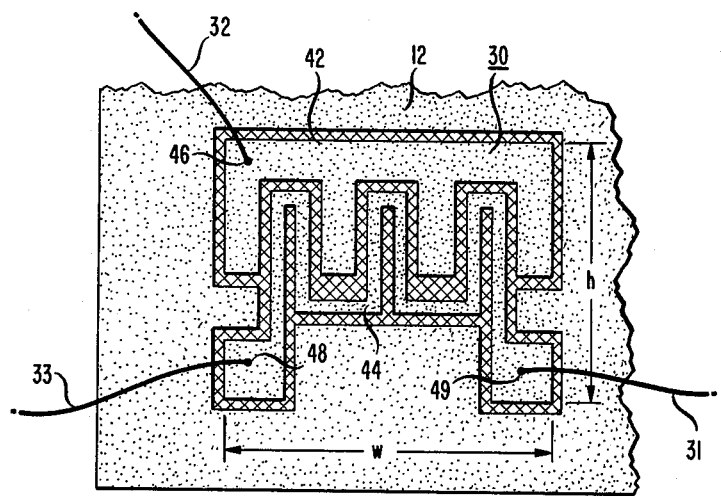
FIG. 2 is a more detailed depiction of one specific illustrative type of sensing unit suitable for inclusion in the FIG. 1 package.

FIG. 2 is a detailed representation of the specific illustrative three-terminal moisture sensing unit 30 shown in FIG. 1. In FIG. 2, the cross-hatched channels designate portions of an underlying ceramic substrate upon which a uniform gold film was initially deposited. The depicted channels were formed by removing gold from the cross-hatched portions.

The unit 30 of FIG. 2 comprises an interdigitated capacitor and a serpentine temperature sensing element. The respective plates of the capacitor are gold regions 42 and 44. Terminal or bonding pad 46 on the region 42 is electrically connected to one end of the aforespecified wire lead 32. The serpentine region 44 includes terminals or bonding pads 48 and 49 near the respective ends thereof. These latter two terminals are also connected to aforespecified wire leads, as shown in FIG. 2.

In one specific illustrative embodiment of the principles of the present invention, the width w of the three-terminal unit 30 shown in FIG. 2 was approximately two millimeters. In that embodiment, the height h was approximately four millimeters. Once the three-terminal unit 30 shown in FIG. 2 and its associated integrated circuit chip 10 are sealed within the package shown in FIG. 1, access to the capacitor is realized by means of exterior terminals 39 and 40 or 39 and 38 (FIG. 1). Access to the temperature sensing element is realized by means of exterior terminals 38 and 40.

In accordance with another specific aspect of the principles of the present invention, only a localized external portion of the package containing the aforedescribed unit 30 is cooled during a moisture measuring cycle. Illustratively, in one advantageous embodiment this is facilitated by providing a blind hole or recessed portion in the exterior wall of the integrated circuit package in direct registry with the unit 30.

Figure 3:
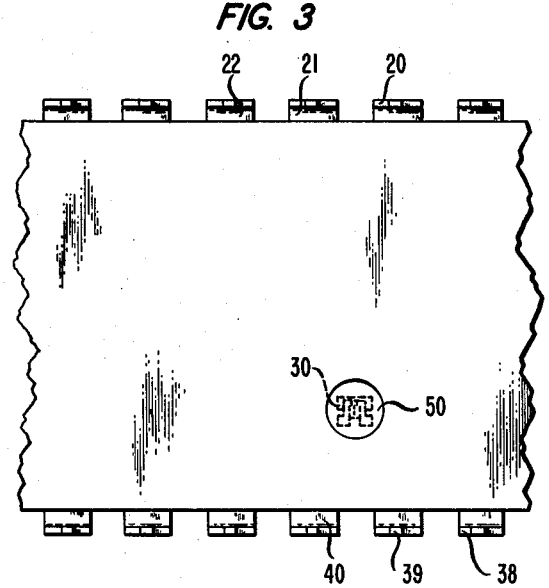
FIG. 3 is a view of a portion of the underside of the FIG. 1 package showing a recessed surface region located in aligned registry with the sensing unit and adapted to receive a cooling head.

Thus, as depicted in FIG. 3, a recess 50 formed in the underside of the package of FIG. 1 is advantageously located in direct underlying alignment with the aforedescribed unit 30. (The unit 30 is shown in dashed outline in FIG. 3.) In one particular illustrative embodiment, the recess 50 was a round recess approximately three millimeters in diameter and 0.5 millimeters deep. In that particular case, the package wall thickness between the bottom of the recess 50 and the unit 30 was only approximately 0.5 millimeters while the standard wall thickness in the vicinity of the recess 50 was approximately one millimeter.

Figure 4:
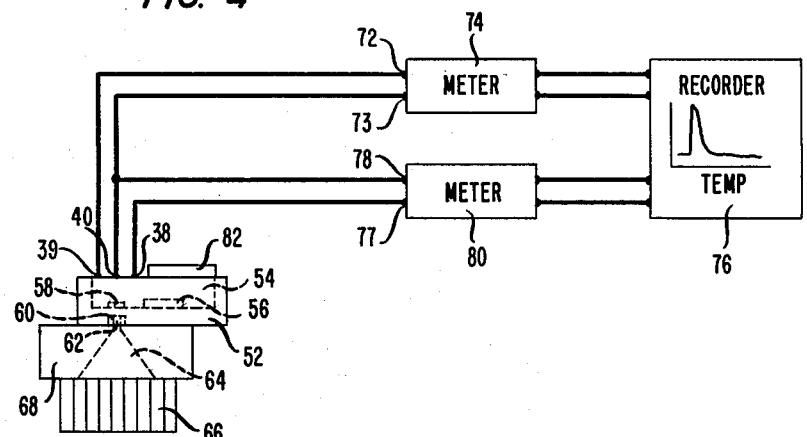
FIG. 4 is a schematic representation of a specific illustrative test arrangement for measuring moisture within a sealed package in accordance with the principles of this invention.

One specific illustrative way in which to implement applicants' moisture measuring method is schematically represented by the arrangement depicted in FIG. 4. As shown therein, a package 52, whose moisture content is to be determined, includes a sealed interior chamber 54 within which are positioned an integrated circuit chip 56 and a three-terminal moisture sensing unit 58 of the type described earlier above. A recess 60 on the bottom side of the package 52 is located in aligned registry with the unit 58. Extending into the recess 60 is a nozzle portion 62 of a standard heat flow concentrator 64 that is mounted on a conventional cooler 66 that is, for example, of the thermoelectric type. Surrounding the concentrator 64 and extending between the package 52 and the cooler 66 is a heat insulating member 68 made, for example, of Teflon (which is a registered trademark of E. I. duPont de Nemours and Co.).

For illustrative purposes, exterior terminals 38 through 40 of the package 52 shown in FIG. 4 are assumed to be connected to the respective terminals of the unit 58 in the same manner specified above in connection with the description of FIGS. 1 through 3. Hence, the capacitance of the interdigitated portion of the unit 58 may be measured between the external terminals 39 and 40, and the resistance of the serpentine temperature sensing portion of the unit 58 may be measured between the terminals 38 and 40.

In accordance with a specific aspect of the principles of the present invention, the external terminals 39 and 40 shown in FIG. 4 are respectively connected to the input terminals 72 and 73 of a meter 74. The meter 74 is a standard unit designed to measure the alternating-current capacitance and/or conductance of the aforedescribed interdigitated portion of the three-terminal unit 58. Illustratively, this measurement is carried out by applying an excitation voltage to the interdigitated element at a frequency in the range of 100 Hertz to 1 megaHertz and sensing the signal caused by a change in capacitance or conductance. (Such an excitation voltage may be supplied either from the meter 74 itself or from a suitable external source.) In turn, the electrical output of the meter 74 is applied to one pair of input terminals of a conventional X-Y recorder 76.

Advantageously, the alternating-current meter 74 of FIG. 4 includes therein a standard phase-sensitive detector. The use of such a detector in making alternating-current measurements is an important basis for achieving a high-noise-rejection characteristic and a high signal-to-noise ratio. Sensitive capacitance and/or conductance measurements of the interdigitated portion of the unit 58 can thereby be made.

The external terminals 38 and 40 shown in FIG. 4 are respectively connected to the input terminals 77 and 78 of a standard resistance measuring meter 80 which measures the direct-current resistance of the serpentine element included in the unit 58. The resistance of the serpentine element varies with temperature. Thus, in a manner known in the art, the electrical output of the meter 80 may be calibrated, for the particular material from which the serpentine element is made, to provide a substantially linear analog signal representative of the temperature of the unit 58 within the package 52. In turn, the output of the meter 80 is applied to a second pair of input terminals of the X-Y recorder 76.

In response to the aforespecified input signals applied thereto, the X-Y recorder 76 of FIG. 4 is adapted to provide a visual display of alternating-current capacitance and/or conductance as a function of temperature. A detailed showing of one specific illustrative such display is depicted in FIG. 5.

Figure 5:
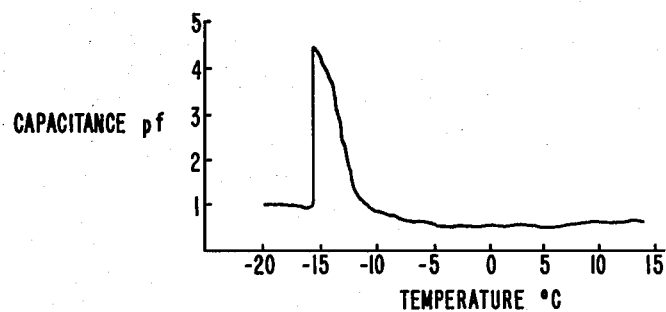
FIG. 5 is a graph showing the relationship between capacitance and temperature as the package of FIG. 4 is cooled during a moisture measuring cycle.

In FIG. 5, the capacitance in picofarads of the interdigitated portion of the aforedescribed sensing unit is plotted as a function of the temperature in degrees centigrade of the serpentine portion of the unit. This plot is characteristic of one particular package whose interior moisture content was measured. As the temperature in the immediate vicinity of the unit 58 (FIG. 4) was decreased at a rate, for example, of about five degrees per minute, the capacitance of the interdigitated element initially remained substantially constant. Subsequently, at a temperature of about $-12$ degrees, an abrupt and sizable increase in capacitance started to occur. The onset of this increase at about $-12$ degrees corresponds with the initial condensation of water on the unit 58, which causes the dielectric constant in the gaps of the interdigitated structure to increase substantially. Hence, the observed initial increase in capacitance occurs at the so-called dew point or dew point temperature of the package being measured.

For each dew point temperature determined in the manner specified above, it is known that the water vapor in the immediate vicinity of the aforementioned condensate is characterized by a specified and exactly determinable partial pressure. Under equilibrium conditions, this same water vapor partial pressure exists throughout the entire volume of the chip-containing compartment 54. Moreover, due to the highly localized nature of the aforespecified cooling of the package 52 (FIG. 4), it is apparent that the temperature within the major part of the compartment 54 differs only slightly from the ambient temperature of the atmosphere surrounding the test equipment shown in FIG. 4. Or a calibrated heating element 82 can advantageously be positioned on the package 52 to establish a major part of the compartment 54 at a specified temperature. Or a standard temperature sensing element can be placed in the compartment 54 to directly monitor the temperature therein at a position that is spaced apart from the unit 58.

By knowing the volume of the compartment 54 and also knowing the partial pressure and the temperature within the major portion of the compartment 54, as discussed above, it is then a straightforward matter to calculate from the ideal gas law the actual number of micrograms of water vapor in the major portion of the compartment.

The localized exterior cooling technique described above and schematically represented in FIG. 4 insures that a measurable amount of the water vapor available within the package under test will condense on the moisture sensing unit. This is especially significant in those situations where the total amount of water vapor within the package is extremely small. If, in such low-moisture cases, the entire exterior of the package were cooled as heretofore proposed, the amount of condensate per unit area on the sensing unit at the dew point would be less than is the case with applicants' localized cooling technique. In some cases of practical importance, this smaller amount of condensate is insufficiently large to cause a clearly detectable increase in the measured capacitance and/or conductance characteristic. Thus, applicants' aforedescribed localized cooling technique is an important basis for achieving a highly sensitive moisture measuring method.

Moreover, applicants have discovered that as the temperature in the vicinity of the sensing unit within the package is further lowered below the dew point, the measured capacitance and/or conductance characteristic continues to increase and then abruptly decreases. Thus, as shown, for example, in FIG. 5, the capacitance value of the aforedescribed interdigitated structure continues to increase and then at a temperature of about $-16$ degrees decreases abruptly. (This particular temperature difference, from $-11$ degrees to $-16$ degrees, is a function of the particular illustrative cooling rate specified above.) It is postulated that this decrease is attributable to the formation of rectifying barriers at ice-to-metal interfaces of the interdigitated structure. In any event, the occurrence of this abrupt decrease immediately following the prior substantial increase is utilized in practice to confirm that the earlier initial increase in capacitance during the cooling cycle (when the curve first trended upward) corresponded in fact to the occurrence of the dew point and was not attributable simply to the occurrence, for example, of a spurious drift in the measuring equipment.

Finally, it is to be understood that the above-described methods and arrangements are only illustrative of the principles of the present invention. In accordance with those principles, numerous modifications and alternatives may be devised by those skilled in the art without departing from the spirit and scope of the invention. Thus, for example, rather than including a sensing unit in every integrated-circuit-containing package of a batch of packages being fabricated, it is advantageous in some cases to include a unit in an otherwise empty package to provide a single test package for each such batch. In that way, the test package may be utilized to monitor the process being utilized to make the entire batch of packages.

Further, although emphasis herein-above has been directed to a particular illustrative sensing unit machined in the bottom of an integrated-circuit package, it is apparent that various modifications and alternative placements of such a unit are feasible. For example, a sensing unit may advantageously be formed in any one of a number of standard ways on the inside surface of the cover 24 (FIG. 1). By providing suitable through-connectors in such a cover, electrical connections can thereby be made to the unit from associated external testing equipment. In such a case, it may also be advantageous to include a recess in the outside surface of the cover to facilitate localized exterior cooling of the sensing unit.

And, of course, the principles of the present invention are not limited to packages designed to house integrated circuits. These principles are manifestly applicable in general to the problem of moisture detection with a sealed package, whatever the nature of the component or assembly contained within the package.

We claim:
1. An electrical assembly comprising
   a housing (52, FIG. 4),
   an interior sealed compartment (54, FIG. 4) defined by said housing,
   plural conductive elements (17 through 22 . . . 35 through 40, FIG. 1) mounted in said housing, each of said elements having an interior end extending into said compartment and an exterior end extending outside of said housing,
   and a moisture sensing unit (30, FIG. 1 or 58, FIG. 4) mounted in said compartment,
   said assembly being CHARACTERIZED IN THAT said housing includes an exterior recess (50, FIG. 3 or 60, FIG. 4) in close proximity to and in aligned registry with said unit, said recess being adapted to receive therein a cooling head (62, FIG. 4).
2. An assembly as in claim 1 further CHARACTERIZED IN THAT said unit comprises first and second spaced-apart conductive members (42, 44, FIG. 2),
   and IN THAT said first conductive member (42) is electrically connected to the interior end (36, FIG. 1) of one of said conductive elements and the ends of said second conductive member (44) are respectively connected to the interior ends (35, 37, FIG. 1) of two other conductive elements.
3. An assembly as in claim 2 further CHARACTERIZED IN THAT the exterior end (39, FIG. 1) of said one conductive element and one of the exterior ends (38 or 40, FIG. 1) of said other conductive elements are respectively connected to the input terminals of an alternating-current capacitance and/or conductance measuring meter (74, FIG. 4),
   and IN THAT the exterior ends (38, 40, FIG. 1) of said other conductive elements are respectively connected to the input terminals of a direct-current resistance measuring meter (80, FIG. 4).
4. An assembly as in claim 3 still further CHARACTERIZED IN THAT the output terminals of said meters (74, 80, FIG. 4) are connected to the input terminals of an X-Y recorder unit (76, FIG. 4).
5. An assembly as in claim 4 still further CHARACTERIZED IN THAT a cooling unit (66, FIG. 4) has mounted thereon a concentrator element (64, FIG. 4) having a cooling head (62, FIG. 4) that extends into the recess (50, FIG. 3 or 60, FIG. 4) in said housing.
6. An electrical assembly comprising
   a housing (52, FIG. 4),
   an interior sealed compartment (54, FIG. 4) defined by said housing,
   plural conductive elements (17 through 22 . . . 35 through 40, FIG. 1) mounted in said housing, each of said elements having an interior end extending into said compartment and an exterior end extending outside of said housing,
   and a moisture sensing unit (30, FIG. 1 or 58, FIG. 4) mounted in said compartment,
   said unit comprising first and second spaced-apart conductive members (42, 44, FIG. 2),
   said assembly being CHARACTERIZED IN THAT said first conductive member (42) is electrically connected to the interior end (36, FIG. 1) of one of said conductive elements and the ends of said second conductive member (44) are respectively connected to the interior ends (35, 37, FIG. 1) of two other conductive elements.
7. A method for measuring the moisture content of the atmosphere within a sealed compartment of known volume that contains therein a sensing unit that includes two spaced-apart conductive members, said method comprising the steps of
   decreasing the temperature within said compartment by cooling only a localized exterior portion of said compartment in close proximity to said sensing unit thereby to condense moisture preferentially on said unit when the dew point of said atmosphere is reached,
   measuring the alternating-current capacitance and/or conductance between the members of said unit as the temperature is decreased below the normal ambient temperature of said compartment,
   detecting the temperature at which the capacitance and/or conductance of said unit initially rises above the value that is characteristic of said unit at the normal ambient temperature,
   and calculating the moisture content of said package from said detected temperature which is the dew point of the atmosphere within said package.
8. A method as in claim 7 further including the step of measuring the direct-current resistance of one of said members in said unit as the temperature is decreased thereby to obtain a measure of the interior temperature of said package in the immediate vicinity of said conductive members.
9. A method as in claim 8 wherein said calculating step comprises
   determining, from said detected dew point temperature, the partial pressure of the water vapor within said compartment,
   and, knowing (1) said partial pressure, (2) the volume of said compartment, and (3) the temperature of the major portion of said compartment, calculating the actual number of grams of water vapor in said compartment.

* * * * *